United States Patent [19]

Quimby

[11] Patent Number: 4,517,824

[45] Date of Patent: May 21, 1985

[54] SOLVENT DUMPING APPARATUS

[75] Inventor: Bruce D. Quimby, Landenberg, Pa.

[73] Assignee: Hewlett-Packard Company, Palo Alto, Calif.

[21] Appl. No.: 510,127

[22] Filed: Jul. 1, 1983

[51] Int. Cl.³ .............................................. G01N 31/08
[52] U.S. Cl. ........................................ 73/23; 73/23.1; 137/239
[58] Field of Search ...................... 73/23, 23.1; 422/89, 422/91; 55/197, 386; 137/239, 597

[56] References Cited

U.S. PATENT DOCUMENTS 3,985,016 10/1976 Haruki ................................. 73/23.1
4,359,891 11/1982 Ahlstrom, Jr. et al. .............. 422/89

Primary Examiner—Stephen A. Kreitman
Attorney, Agent, or Firm—Donald N. Timbie

[57] ABSTRACT

A solvent dumping apparatus is described having an inlet enclosure coupled to the inlet of a detector and an outlet enclosure coupled to the outlet of a detector. Venting means are provided for both enclosures, one of which is controllable; means are provided for introducing sample gas into the inlet enclosure; and means are provided for introducing gas into the outlet enclosure. During a detection mode, at least one of the venting means is so adjusted as to cause sample gas to flow through the detector and out the venting means for the outlet enclosure, and during a diversionary mode, at least one of the venting means is so adjusted as to cause the gas introduced into the outlet enclosure to pass back through the detector and carry any sample gas out through the venting means for the inlet enclosure. In preferred forms of the invention, one of the venting means is a back pressure regulator.

12 Claims, 9 Drawing Figures

SOLVENT DUMPING APPARATUS

BACKGROUND OF THE INVENTION

In preparing certain materials for analysis by a gas chromatograph, it is often necessary to mix them with a solvent. Unfortunately, however, when material prepared in this manner is injected into the stream of carrier gas entering a gas chromatographic column, the concentration of the solvent in the sampling gas eluting from the other end of the column is usually so great as to cause some types of detectors connected to the output of the column to malfunction, e.g., an atomic emission detector. Apparatus for permitting sample gas to flow through the detector during a detection mode and for diverting the portion of the flow of sample gas containing the solvent to a vent during a diversionary mode so as to prevent it from reaching the detector is described by Messrs. Scott A. Estes, Peter C. Uden and Ramon M. Barnes in an article entitled "High Resolution Gas Chromatography of Trialkyllead Chlorides with an Inert Solvent Venting Interface for Microwave Excited Helium Plasma Detection", published in *Analytical Chemistry*, Vol. 53, No. 9, August 1981. Since all of the components of the solvent dumping apparatus are on the inlet side of the detector, it has the following disadvantages:

(a) The large surface area that lies between the end of the chromatographic column and the inlet of the detector must be deactivated if polar or reactive materials are to be analyzed.

(b) Unwanted peaks are produced in the output signals from the detector as a result of some solvent adsorbing on the relatively large surface area over which sample gas must flow during the diversionary mode and the subsequent removal of this adsorbed solvent by the make-up gas during the following detection mode.

(c) It is difficult to maintain the pressure at the end of the chromatographic column the same during the detection and diversionary modes of operation for different rates of sample flow.

BRIEF SUMMARY OF THE INVENTION

In accordance with the invention, the solvent dumping apparatus for a detector is comprised of an inlet enclosure having a port that can be coupled to the entrance of a detector and an outlet enclosure having a port that can be coupled to the exit of a detector. The inlet enclosure has venting means and means for permitting sample gas to be introduced therein, and the outlet enclosure has venting means and means for permitting gas to be introduced therein. The use of the two enclosures reduces the amount of surface area that should be deactivated and permits control of the environment at the exit of the detector so as to prevent air from diffusing into the detector. The inlet volume may be made small enough to make the use of make-up gas unnecessary if packed or large capillary columns are used, but if the sample gas is introduced via a small capillary tube, the inlet enclosure may be provided with means for permitting make-up gas to be introduced therein. For reasons which will be explained, if make-up gas is used, the point where it is introduced into said inlet enclosure is farther away from the output port thereof than the point where the sample gas is introduced. In preferred embodiments, the venting means for one of the inlet and outlet enclosures is a back pressure regulator and the venting means for the other enclosure is a controllable valve. Preferably, the back pressure regulator is coupled to the inlet enclosure, but in either case it acts as a safety pressure release and makes it easier to maintain the pressures at the end of the columns the same during the detection and diversionary modes. If the detector operates by measuring the intensities of different wavelengths of light emanating from the exit, the outlet enclosure is provided with a window through which the light can pass, and preferably the venting means of the outlet enclosure and the means for permitting gas to be introduced therein are on opposite sides of the window so that gas can pass over the window on its way to the venting means during the detection mode and reduce the rate at which material emerging from the exit of the detector is deposited thereon. Although the various embodiments of the solvent dumping apparatus of this invention will be described in conjunction with an atomic emission detector, it will be understood that it can be advantageously used with other detectors, including a photoionization detector and a nitrogen phosphorous detector.

In order for the apparatus to be in a detection mode, the ratio of the hydraulic resistance of the venting means for the inlet enclosure to the hydraulic resistance of the venting means for the outlet enclosure has to be increased so that sample gas introduced into the inlet enclosure will flow through a detector mounted between the ports of the inlet and outlet enclosures and out of the venting means for the outlet enclosure.

In order for the apparatus to be in a diversionary mode, the ratio of the hydraulic resistance of the venting means for the inlet enclosure to the hydraulic resistance of the venting means for the outlet enclosure has to be decreased so that gas introduced into the outlet enclosure will flow back through the detector and carry any solvent contained in the sample gas through the inlet enclosure and out of its venting means.

DESCRIPTION OF THE PRIOR ART

Figure 1:
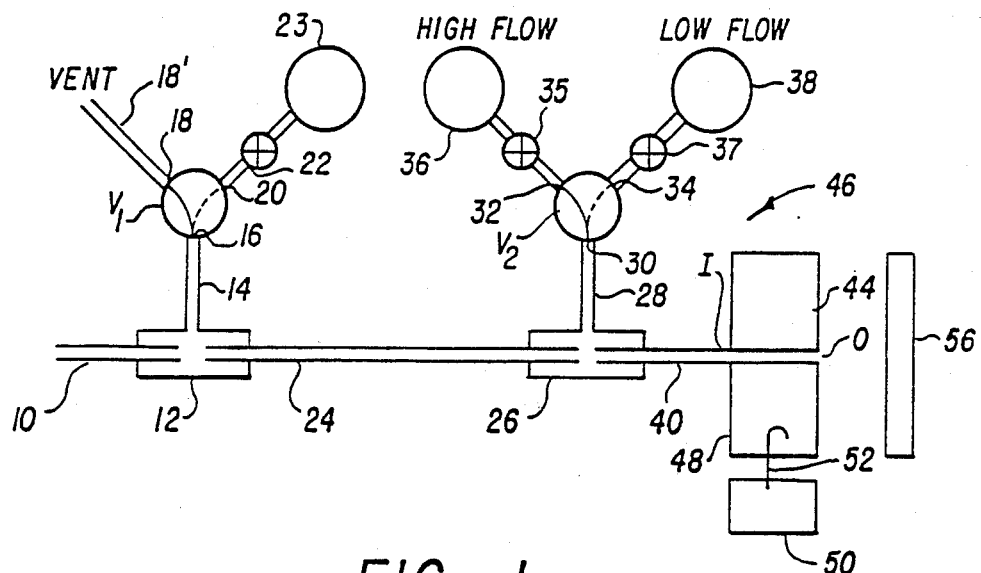
FIG. 1 is a schematic representation of solvent dumping apparatus of the prior art.

In the apparatus of the prior art shown in FIG. 1, a chromatographic column 10 is inserted in one end of a straight-through passage 12 of a first T coupling, and the stem 14 of the T coupling is connected to a common port 16 of a two-way valve $V_1$ that can selectively connect its common port 16 to a port 18 or a port 20. The port 18 is connected to vent by a tube 18'. When the word "vent" is used at any point in the application, it will be understood to be the atmosphere or controlled environment. The port 20 is connected by a valve 22 to a source 23 of pressurized make-up gas. A tube 24 connects the straight-through passage 12 of the first T coupling to a straight-through passage 26 of a second T coupling. The stem 28 of the second T coupling is connected to a common port 30 of a two-way valve $V_2$ that can selectively connect its common port 30 to a port 32 or a port 34. The port 32 is coupled via a valve 35 to a pressurized source 36 of make-up gas. The port 34 is coupled via a valve 37 to a pressurized source 38 of make-up gas. The valves 35 and 37 are adjusted so that when it occurs the flow of make-up gas from the former is greater than the flow from the latter.

A tube 40 connects the straight-through passage 26 of the second T coupling to the inlet I of a tube 44 defining the detection zone of an atomic emission detector 46. The tube 44 is mounted in a cavity 48, and radio frequency energy is coupled into the cavity 48 from a source 50 by a probe 52. The radio frequency energy causes a discharge in the discharge tube 44 that breaks down the gases therein into their atomic components. As each atom is formed, it emits its characteristic wavelengths of light. The intensity of each wavelength of light emanating from the outlet O of the discharge tube 44 is measured by a means 56 so as to provide information from which the relative amounts of each atom of the gas in the discharge tube can be determined. With this type of detector as well as others, the presence of a large relative amount of solvent in the carrier gas in the detection zone defined by the tube 44 can extinguish the discharge occurring therein so as to make the detector inoperative.

When the solvent dumping apparatus of FIG. 1 is being operated in its detection mode, the valve $V_1$ is set so as to close off communication between vent and the common port 16 and to provide communication between the common port 16 and the source 23 of pressurized make-up gas; and the valve $V_2$ is set so as to close off communication between the common port 30 and the source 36 of pressurized make-up gas and to provide communication between the common port 30 and the source 38 of pressurized make-up gas. The flow of make-up gas from the source 23 is adjusted so as to keep the linear velocity of gas in the tube 24 the same as the linear velocity of sample gas eluting from the column 10; and the minimum flow of make-up gas from the source 38 is adjusted so as to keep the sample gas from entering the passage 26 or the stem 28. Additional gas may be required to keep the linear velocity of flow in the tube 44 the same as that eluting from the column 10.

When the solvent dumping apparatus of FIG. 1 is being operated in its diversionary mode, the valves $V_1$ and $V_2$ are set in their other positions so that the stem 14 of the first T coupling is connected to vent and the stem 28 of the second T coupling is connected so as to receive the higher flow of make-up gas from the source 36. Part of the gas from the stem 28 flows back through the tube 24 and carries sample gas eluting from the column 10 up through the stem 14 of the first T coupling and via ports 16 and 18 and the tube 18' to vent. The other part of the gas from the stem 28 flows through the tube 40 so as to pass through the detection zone 44. If the detector is of the atomic emission type, the latter flow is necessary in order to maintain the discharge, but if it is too great, it can extinguish the discharge.

From an inspection of FIG. 1, it can be seen that there is a great deal of surface between the end of the column 10 and the inlet I of the detector that must be deactivated if polar or reactive materials are to be analyzed. It will be observed that during the diversionary mode of operation some of the solvent will be adsorbed in the stem 14 of the first T coupling as well as the seat of the valve $V_1$, and that during the subsequent detection mode, make-up gas from the source 23 will pick up some of the solvent as it passes through the valve $V_1$ and the stem 14 so as to cause an undesired peak to be produced in the output signal of the detector.

For reasons that will be understood by those skilled in the art, it is desirable to keep the pressure at the end of the column 10 the same for both modes of operation. In order to reverse the flow of sample gas in the tube 24 during a diversionary mode, practicable considerations require that the tube 40 have some finite hydraulic resistance. It can be seen, for example, that if its hydraulic resistance and that of the tube 44 were negligible, it would require a very high flow of gas from the source 36 to build up a pressure across this resistance that would be greater than the pressure at the end of the column 10, as is required if the flow of sample gas is to be reversed. Furthermore, if the detector is of the atomic emission type, the large flow of gas passing through it under these conditions might well extinguish the discharge in the tube 44 that is necessary for detection. Assuming then that the hydraulic resistance of the tube 40 is such as to permit reasonable flows of gas from the source 36 to be used, it will be necessary to adjust the hydraulic resistance of the system between vent and the adjacent ends of the column 10 and the tube 24 so as to maintain the pressure at the end of the column 10 the same as it was in the detection mode. Assume that the system has been adjusted in this manner when the column 10 is a small capillary tube having a small sample gas flow and that a packed column having a much larger sample gas flow is used. It will be found that the hydraulic resistance of the tube 40 should be changed. This is far from convenient because the tube 40 is part of the system through which sample gas passes.

DETAILED DESCRIPTION OF THE INVENTION

All the figures of the drawings are schematic in that they represent cross-sections of gas chromatographic detection apparatus. In all the figures, corresponding components are designated by the same numerals or letters. Whereas the figures of the drawings all show an atomic emission detector, it is to be understood that other types of detectors having an inlet, outlet and detection zone could also be used.

Figure 2:
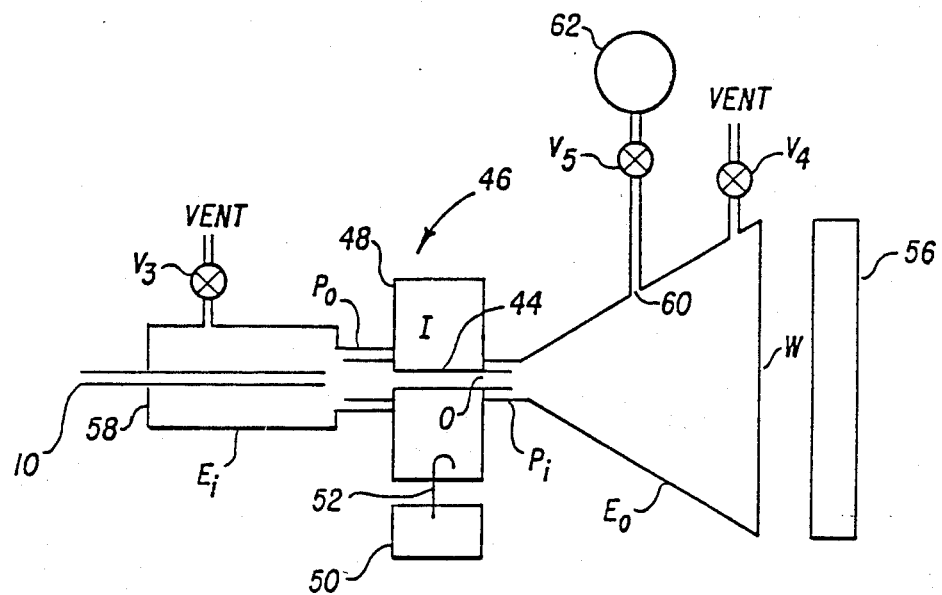
FIG. 2 is a schematic representation of an embodiment of the invention not using make-up gas.

FIG. 2 illustrates a solvent dumping apparatus constructed in accordance with a basic aspect of the invention. It is comprised of an inlet enclosure $E_i$ having an outlet port $P_o$, a venting means, herein shown as being a valve $V_3$ coupled to the input enclosure $E_i$, means for permitting sample gas to be introduced into the input enclosure $E_i$, herein shown as being an aperture 58 through which the column 10 can be inserted, and an outlet enclosure $E_o$ having an inlet port $P_i$, a venting means in the form of a valve $V_4$ coupled between the enclosure $E_o$ and vent, and means for permitting gas to be introduced therein, herein shown as being an aperture 60. In operation, a source 62 of pressurized gas is coupled by a valve $V_5$ to the aperture 60. If the detector responds to light, a window W forms one wall of the outlet enclosure $E_o$. When the solvent dumping apparatus is in use, a detector is mounted with its inlet I sealingly coupled to the outlet port $P_o$ and its outlet sealingly coupled to the inlet port $P_i$. The structure just described is all that is required for solvent dumping in accordance with the basic aspect of the invention.

During a detection mode, the valve $V_3$ is closed, the valve $V_4$ is open, and the valve $V_5$ may be open or closed so that sample gas eluting from the column 10 passes through the detection zone in the tube 44, through the outlet enclosure $E_o$ and out to vent via the valve $V_4$.

During the diversionary mode, the valve $V_3$ is open, the valve $V_4$ is closed, and the valve $V_5$ is open so that gas from the source 62 reverses the flow of sample gas, causing it to go out to vent via the valve $V_3$.

It is to be noted that there is very little, if any, interior surface between the end of the column 10 and the inlet I of the detector 46 so that little deactivation is required. Furthermore, the various valves can be adjusted so as to achieve the proper flows during both modes of operation for columns having different flow rates, thereby making it unnecessary to change any of the hardware.

Figure 3:
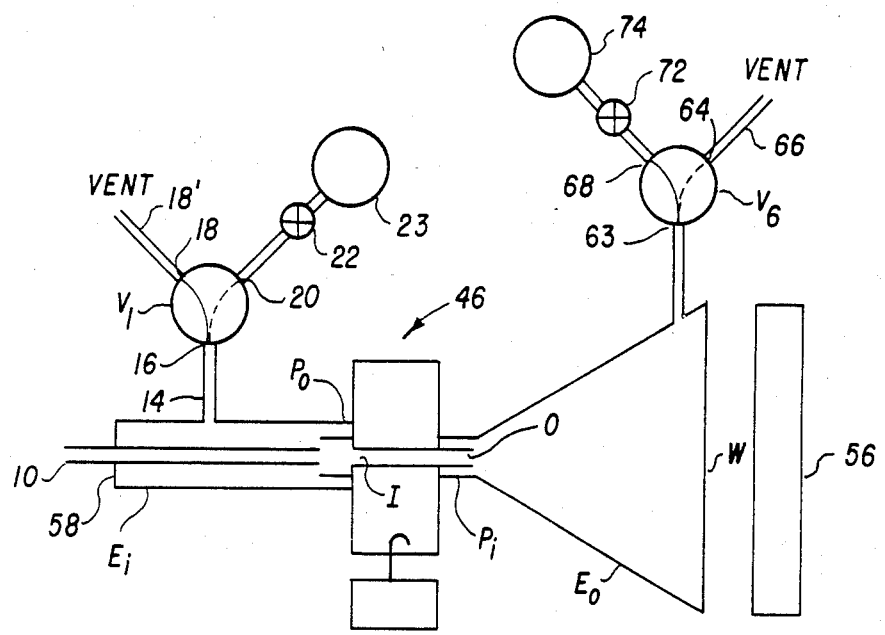
FIG. 3 is a schematic representation of an embodiment of the invention having a two-position valve for placing the inlet enclosure in communication with a source of pressurized make-up gas or with a vent, and also having a two-position valve for placing the outlet enclosure in communication with a vent or with a source of pressurized gas.

In order to prevent sample gas from diffusing into the inlet enclosure $E_i$ during the detection mode and causing unwanted peaks during the output signal of the detector, means are provided for permitting make-up gas to be introduced into the inlet enclosure $E_i$ as shown in FIG. 3. Furthermore, quite apart from this problem, make-up gas may be required in order to maintain the velocity of the sample gas through the detector 46 at a desired level when the column 10 is such as to have a very low elution flow, e.g., a capillary column with a small inner diameter. Whereas make-up gas could be introduced through a separate valve, it is convenient to use a valve assembly such as $V_1$ of FIG. 1 that permits make-up gas to flow into the inlet enclosure $E_i$ when in one position and permits sample gas to flow out of it to vent when in the other position. The apparatus of FIG. 3 could utilize the valves $V_4$ and $V_5$ of FIG. 2 for its outlet enclosure $E_o$, but it is shown as having a single two-position valve $V_6$ with its common port 63 coupled to the outlet enclosure $E_o$. The venting means for the outlet enclosure $E_o$ includes the common port 63 and a selectable port 64 which is coupled to vent via a tube 66, and the means for permitting gas to enter the outlet enclosure $E_o$ includes the common port 63 of the valve $V_6$, its other selectable port 68 and a valve 72 that is coupled to a source 74 of pressurized gas. Operation in the detection and diversionary modes is essentially the same as that of FIG. 2 except that gas from the source 74 does not enter the outlet enclosure $E_o$ during the detection mode because the common port 63 of the valve $V_6$ does not communicate with the selectable port 68.

Figure 4:
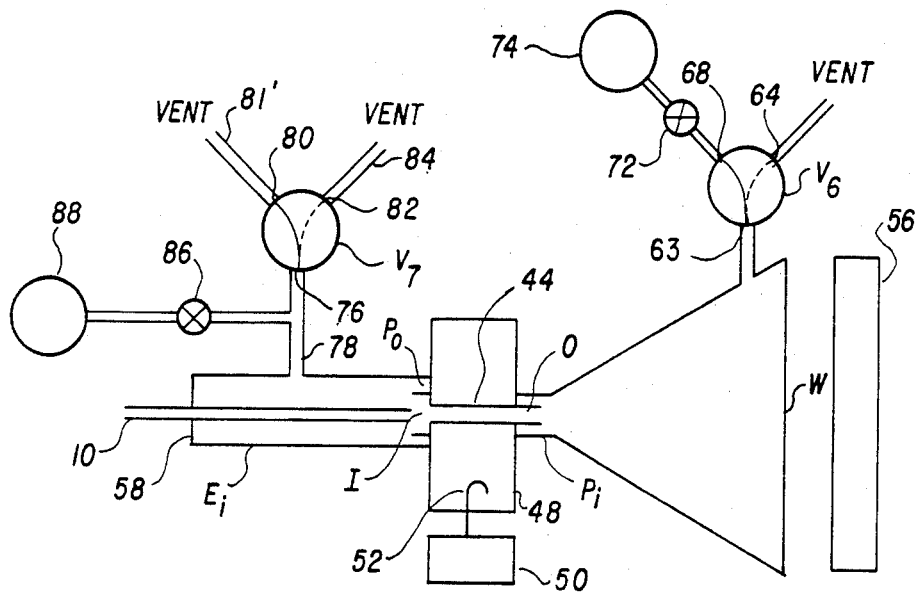
FIG. 4 is like FIG. 3 except that the two-position valve for the inlet enclosure places it in communication with a restricted vent or with a vent and a source of make-up gas continuously coupled to said inlet enclosure.

From an examination of FIG. 3, it can be seen that solvent can be adsorbed by the tube 14 and the valve $V_1$ during the diversionary mode. In order to eliminate the adsorption of the valve $V_1$ and part of the tube 14, an arrangement such as shown in FIG. 4 could be used in which the venting means for the inlet enclosure $E_i$ is comprised of a two-position valve $V_7$ having a common port 76 that is coupled via a tube 78 to the inlet enclosure $E_i$, a selectable port 80 that is coupled to vent and a selectable port 82 that is coupled to vent via a restricted tube 84. The means for introducing make-up gas to the inlet enclosure $E_i$ is part of the tube 78 and a valve 86 coupled between it and a source 88 of pressurized make-up gas. The means for venting the outlet enclosure $E_o$ and for permitting gas to be introduced into it are the same as in FIG. 3. Any solvent that adheres during the diversionary mode to the valve $V_7$ or to the portion of the tube 78 between its common port 76 and the point on it to which the valve 86 is coupled is not carried into the detector during the following detection mode.

During the detection mode, the valve $V_7$ is positioned so as to couple the restricted tube 84 to the inlet enclosure $E_i$, and the valve $V_6$ is positioned so as to couple the outlet enclosure $E_o$ to vent. Some make-up gas will be flowing out the restricted tube 84 all the time so as to carry away adsorbed solvent, and some make-up gas will flow along with sample gas through the detector and the outlet enclosure and out to vent via the valve $V_6$.

During the diversionary mode, the valve $V_7$ is positioned so as to couple the inlet enclosure $E_i$ to vent 80' and the valve $V_6$ is positioned so as to couple the outlet enclosure $E_o$ to the source 74 of pressurized gas.

Figure 5:
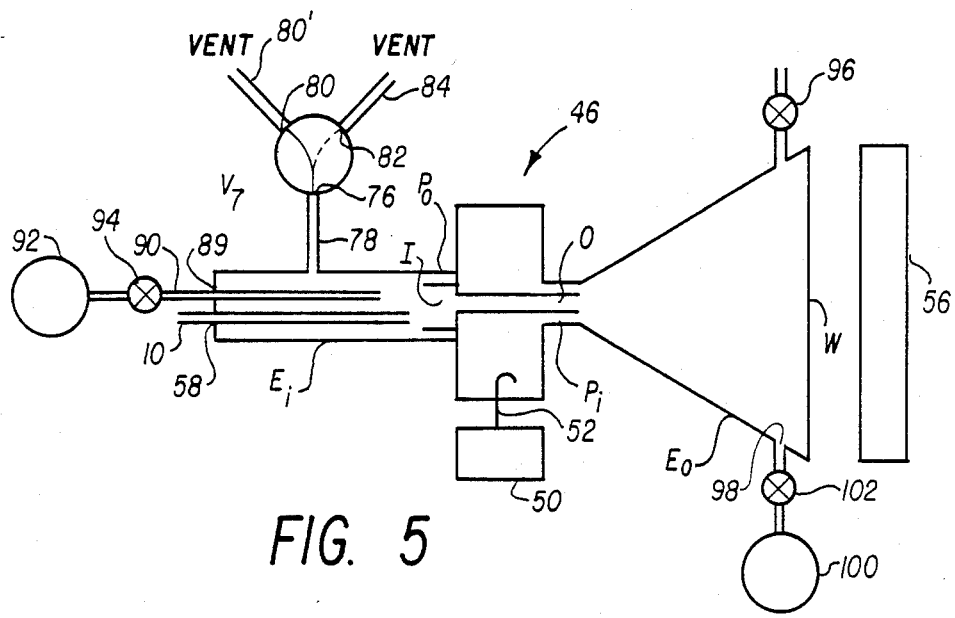
FIG. 5 is a schematic representation of an embodiment of the invention having a two-position valve for placing the inlet enclosure in communication with a vent or a restricted vent, a tube for sample gas and a tube for make-up gas inserted through said inlet enclosure, a valve for placing the outlet enclosure in communication with vent and a source a pressurized gas continuously coupled to the outlet enclosure.

In accordance with another aspect of this invention, the means for permitting make-up gas to be introduced into the inlet enclosure $E_i$ is an aperture 89 such as shown in FIG. 5 through which a tube 90 carrying make-up gas from a pressurized source 92 and a valve 94 may be inserted. The venting means for the inlet enclosure $E_i$ is the same as in FIG. 4. By placing the end of the tube 90 farther away from the inlet I of the detector than the end of the column 10, the amount of surface that is traversed in one direction by the solvent during a diversionary mode and then traversed in the other direction during the following detection mode is reduced to such a degree that the amount of adhered solvent carried into the detector 46 during the detection mode is negligible.

FIG. 5 also illustrates a second aspect of this invention by which the window W is prevented from accumulating dirt and reducing the sensitivity of the detector. In fact, the window W could become so dirty in a relatively short time as to make the detector 46 useless. A valve 96 couples the outlet enclosure $E_o$ to vent and the means for permitting gas to be introduced into the outlet enclosure $E_o$ is an aperture 98 that is located opposite the valve 96. In operation, a source 100 of pressurized gas is coupled via a valve 102 to the aperture 98, and the valve 102 is set so as to permit gas to enter the outlet enclosure $E_o$ constantly.

During the detection mode, the valve $V_7$ couples the inlet enclosure $E_i$ to the restricted tube 84 and the valve 96 is open so that sample gas and make-up gas flow through the detector 46 into the outlet enclosure $E_o$ and out the valve 96. At the same time, gas flows from the source 100, through the aperture 98, across the window W and out to vent via the valve 96, thus preventing dirt from accumulating in the window W.

During the diversionary mode, gas from the source 100 flows through the valve 102, the aperture 98, the outlet enclosure $E_o$, the detector 46, the inlet enclosure $E_i$, and out to vent via the tube 78 and the valve $V_7$.

In all of the embodiments of the invention thus far described, the pressure at the end of the column 10 can be kept the same during the detection and diversionary modes by suitable adjustment of the valves controlling the flow of gas into the outlet enclosure and the selection of the proper hydraulic impedance for the venting means for the inlet enclosure. With respect to this, note that although the tubes to vent such as 18' and 80' did not show a resistance, they inherently have one that can be designed to have the proper value. No hardware has to be replaced but different adjustments and valves may be required for columns having different flow rates.

This problem is overcome in accordance with a third aspect of the invention by using a back pressure regulator as the venting means for either the inlet enclosure $E_i$ or the outlet enclosure $E_o$. Such an arrangement is illustrated in the preferred embodiment of FIG. 6 that is the same as FIG. 5 except that a back pressure regulator 104 is substituted for the valve $V_7$ and is therefore the means for venting the inlet enclosure $E_i$. If make-up gas were not used, a portion of the sample gas would have to pass through the back pressure regulator 104 to make it operable.

Figure 6:
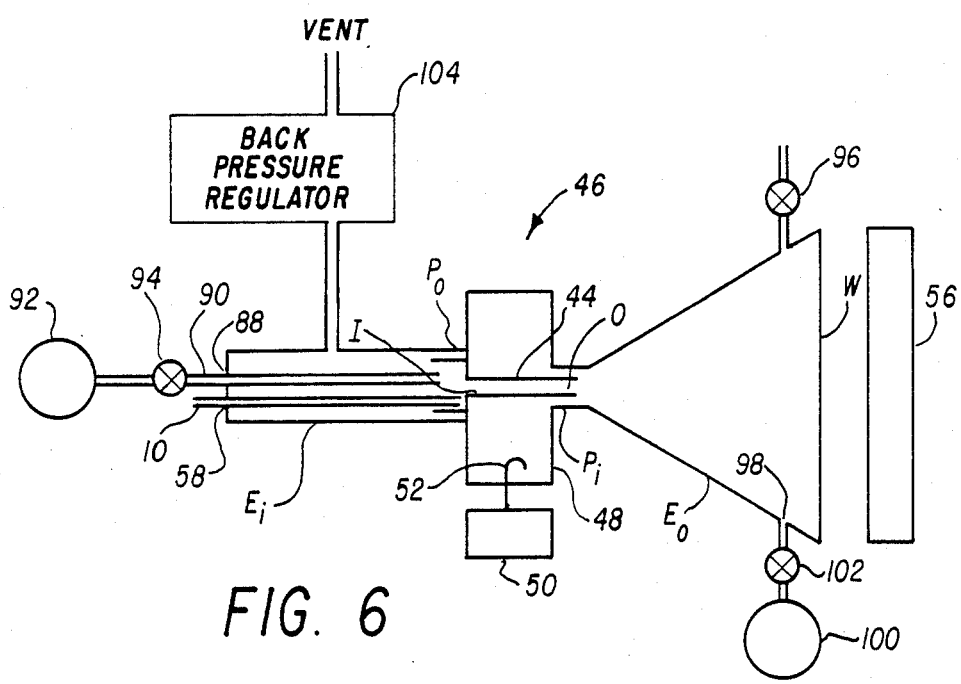
FIG. 6 is like FIG. 4 except that a back pressure regulator is substituted for the valve that controls communication between the inlet enclosure and the vent.
Figure 7:
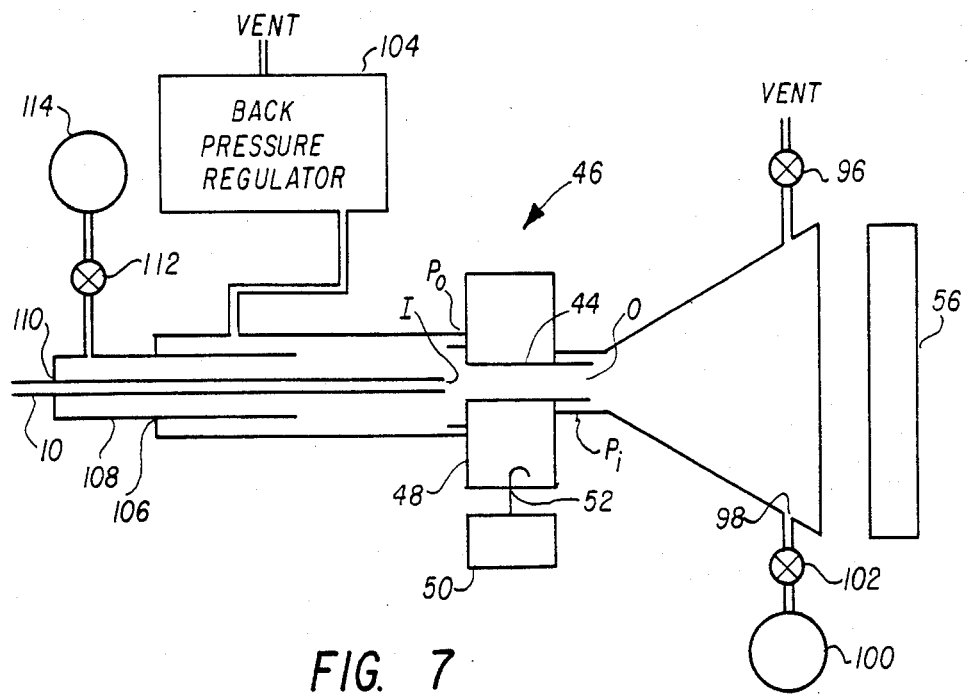
FIG. 7 is a schematic representation of one form of a preferred embodiment of this invention in which coaxial tubes respectively introduce sample gas and make-up gas to the inlet enclosure, a back pressure regulator is the venting means for the inlet enclosure, a valve places the outlet enclosure in communication with vent, and a source of pressurized gas is coupled to the outlet enclosure.

FIG. 7 is an alternative form of the preferred embodiment of the invention of FIG. 6 that has some advantages in the fabrication of the means for introducing sample gas and make-up gas to the inlet enclosure $E_i$. The means for permitting sample gas to be introduced into the inlet enclosure $E_i$ and the means for permitting make-up gas to be introduced into the inlet enclosure $E_i$ is an aperture 106 which permits a tube 108 to be passed through it. The tube 108 is closed at one end except for an aperture 110 and is coupled via a valve 112 to a pressurized source 114 of gas, and the column 10 is inserted through the aperture 110 so as to be concentric with the tube 108. As in other embodiments, the column 10 is nearer the inlet I of the detector 46 than the end of the tube 108 carrying make-up gas.

As previously mentioned, the back pressure regulator 104 may be coupled to the outlet enclosure $E_o$. Whereas this may not control the pressure at the end of the column 10 as accurately as when the back pressure regulator is coupled to the inlet enclosure $E_i$, there is an advantage that none of the solvent gas need pass through it.

Figure 8:
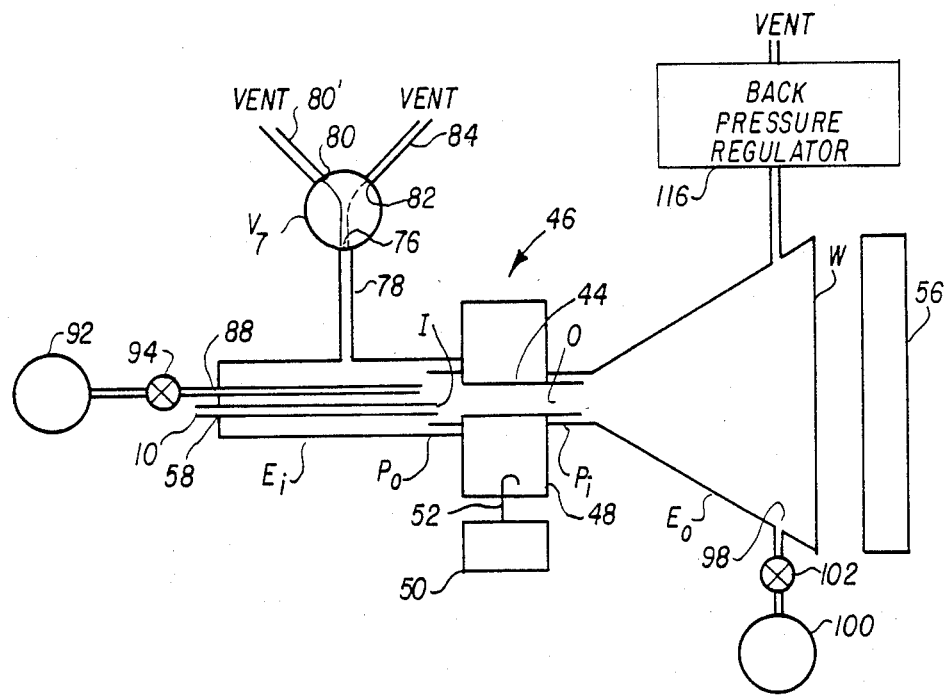
FIG. 8 is a schematic representation of a preferred embodiment of this invention having tubes for introducing sample gas and make-up gas to the inlet enclosure, a two-position valve for placing the inlet enclosure in communication with vent or a restricted vent, a back pressure regulator is the venting means for the outlet enclosure, and a source of pressurized gas is coupled to the outlet enclosure.

Reference is now made to FIG. 8 which is like FIG. 6 in the way by which sample gas and make-up gas are introduced into the inlet enclosure $E_i$. It differs, however, in that the means for venting the inlet enclosure $E_i$ is a two-position valve such as used in FIGS. 4 and 5, and also in the replacement of the valve 96 of FIG. 6 with a back pressure regulator 116.

During the detection mode, the valve $V_7$ of FIG. 8 is positioned to couple the inlet volume to the restricted tube 84 so that the sample gas and make-up gas, if present, can pass through the detector and the outlet enclosure $E_o$ and through the back pressure regulator to vent. During the diversionary mode, the valve $V_7$ is positioned to couple the inlet enclosure $E_i$ to vent. Gas from the source 100 flows through the back pressure regulator 116 so as to maintain the pressure in the outlet enclosure $E_o$ at the same value as when sample gas was flowing through it. The gas also flows back through the detector 46 to the inlet enclosure $E_i$ and carries any solvent with it through the valve $V_7$ and out to vent. Because of the hydraulic resistance of the tube 44, there is a slight pressure drop from the inlet I of the detector to its outlet O during the detection mode so that the pressure at the end of the column 10 is slightly higher than it is at the pressure regulator 116. During the diversionary mode, there is a slight pressure drop between the output O of the detector and its inlet I so that the pressure at the end of the column 10 is slightly less than that at the pressure regulator 116. For these reasons, the pressure at the end of the column 10 is slightly higher during the detection mode than it is during the diversionary mode.

Figure 9:
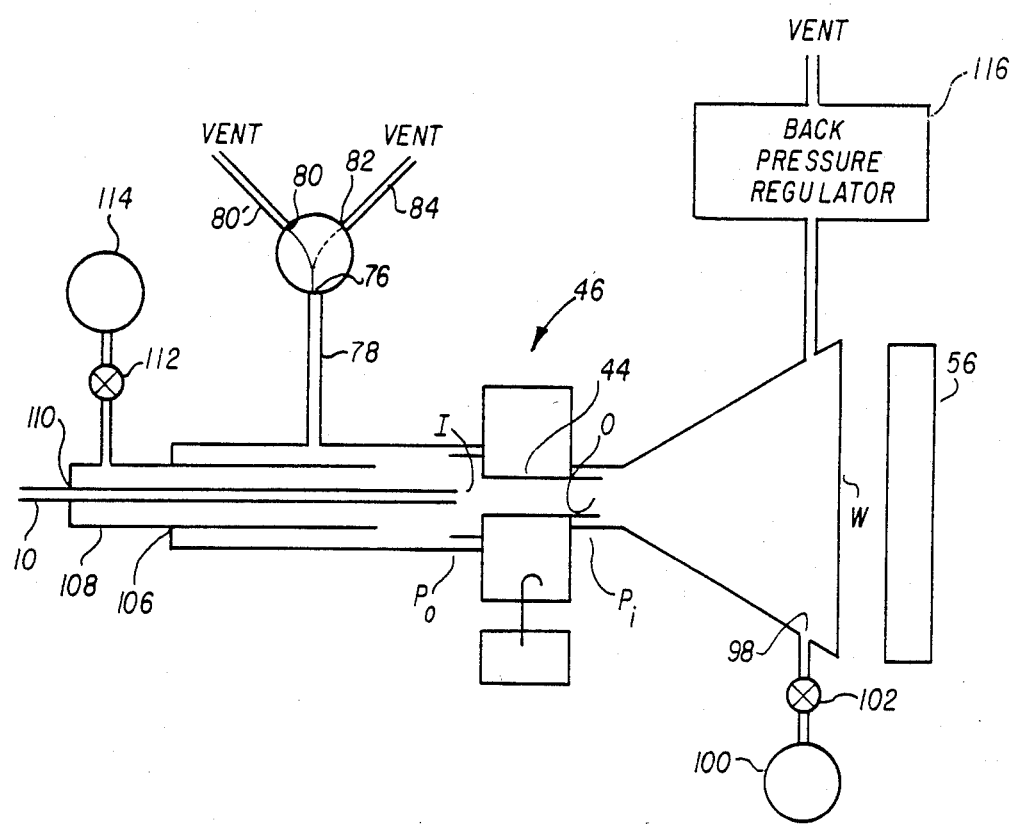
FIG. 9 is a schematic representation of another form of this invention in which a two-position valve places the inlet enclosure in communication with restricted vent and a more restricted vent, coaxial tubes respectively introduce sample and make-up gas to the inlet enclosure, a back pressure regulator is the venting means for the outlet enclosure and a source of pressurized gas is coupled to the outlet enclosure.

FIG. 9 is like FIG. 8 except that the manner in which sample and make-up gases are introduced into the inlet enclosure $E_i$ is the same as in FIG. 7. Otherwise, it operates in the same way as FIG. 8.

What is claimed is:

1. Solvent dumping apparatus for a gas chromatographic detector, comprising
    an inlet enclosure having an outlet port for coupling to the inlet of a detector, said inlet enclosure having venting means and means for permitting sample gas, when present, to be introduced therein,
    an outlet enclosure having an inlet port for coupling to the outlet of a detector, said outlet enclosure having venting means and means for permitting gas, when available, to be introduced therein, and wherein
    at least one of said venting means is controllable.

2. Solvent dumping apparatus as set forth in claim 1 wherein said controllable venting means is a back pressure regulator and one is a valve.

3. Solvent dumping apparatus as set forth in claim 1 wherein means are provided for permitting make-up gas, when available, to be introduced into said inlet enclosure at a point that is more remote from its outlet port than the point at which sample gas, when present, is introduced therein.

4. Solvent dumping apparatus as set forth in claim 1 wherein a detector is provided having an inlet coupled to said outlet port of said inlet enclosure and an outlet coupled to said inlet port of said outlet enclosure.

5. Solvent dumping apparatus as set forth in claim 3 wherein said venting means for said inlet enclosure and the means for permitting make-up gas to be introduced into said inlet enclosure are valve means, and wherein said venting means for said outlet enclosure and the means for permitting gas to be introduced therein are valve means.

6. Solvent dumping apparatus as set forth in claim 1 wherein said venting means for said inlet enclosure is a multi-position valve having a common port coupled by a first tube to said inlet enclosure, a port that communicates with said common port when said valve is in one position coupled to vent and a port that communicates with said common port when the valve is in said another position coupled to a restricted vent, and wherein the means for permitting make-up gas to be introduced into said inlet enclosure is a second tube coupled to said first tube.

7. Solvent dumping apparatus as set forth in claim 1 wherein said venting means for said inlet enclosure is a multi-position valve having a common port that communicates with said inlet enclosure, a port that communicates with said common port when said valve is in one position coupled to a restricted vent, and a port that communicates with said common port when said valve is in another position coupled to said vent,
- wherein the means for permitting sample gas to be introduced into said inlet enclosure is a tube passing through said inlet enclosure to the outlet port thereof, and
- wherein said means for permitting make-up gas to be introduced into said inlet enclosure is a tube passing through said inlet enclosure to a point that is more remote from said outlet port of said inlet enclosure than the end of the tube for introducing sample gas therein.

8. Solvent dumping apparatus as set forth in claim 1 wherein
- said venting means for said inlet enclosure is a back pressure regulator coupled thereto,
- said means for permitting sample gas to be introduced into said inlet enclosure is a tube passing through said inlet enclosure to said outlet port thereof, and
- said means for permitting make-up gas to be introduced into said inlet enclosure is a tube passing through said inlet enclosure to a point that is more remote from said outlet port of said inlet enclosure than the end of said tube for introducing sample gas therein.

9. Solvent dumping apparatus as set forth in claim 1 wherein
- said venting means for said inlet enclosure is a back pressure regulator,
- said means for permitting sample gas to be introduced into said inlet enclosure is a first tube passing through said inlet enclosure to said outlet port thereof, and
- said means for permitting make-up gas to be introduced into said inlet enclosure is a second tube coaxial with said first tube and passing through said inlet enclosure to a point that is more remote from said outlet port of said inlet enclosure than the end of said first tube.

10. Solvent dumping apparatus as set forth in claim 1 wherein
- said venting means for said inlet enclosure is a multi-position valve having a common port communicating with said inlet enclosure, a port that communicates with said common port when said valve is in one position coupled to a restricted vent, and a port that communicates with said common port when said valve is in another position coupled to said vent,
- said means for permitting sample gas to be introduced into said inlet enclosure is a first tube passing through said enclosure to the outlet port thereof,
- said means for permitting make-up gas to be introduced into said inlet enclosure is a second tube coaxial with the first tube and passing through said inlet enclosure to a point that is more remote from said outlet port of said inlet enclosure than the end of said first tube, and
- said venting means for said outlet enclosure is a back pressure regulator.

11. Solvent dumping apparatus as set forth in claim 1 wherein
- said venting means for said inlet enclosure is a multi-position valve having a common port communicating with said inlet enclosure, a port that communicates with said common port when said valve is in one position coupled to a restricted vent, and a port that communicates with said common port when said valve is in another position coupled to said vent,
- said means for permitting sample gas to be introduced into said inlet enclosure is a first tube passing through said enclosure to the outlet port thereof,
- said means for permitting make-up gas to be introduced into said inlet enclosure is a second tube passing through said inlet enclosure to a point more remote from said outlet port thereof than the end of said first tube, and
- said venting means for said outlet enclosure is a back pressure regulator.

12. Solvent dumping apparatus as set forth in any of claims 1 through 11 wherein
- a transparent window is provided in said outlet enclosure, and
- said venting means for said outlet enclosure and said means for permitting gas to be introduced therein are on opposite sides of said window on the way to the venting means, thereby inhibiting the deposition of matter on the inside surface of said window.

* * * * *